(12) United States Patent
Srivastava et al.

(10) Patent No.: US 8,298,591 B2
(45) Date of Patent: Oct. 30, 2012

(54) ANTI-FEVER BOTANICAL COMPOSITION AND USES THEREOF

(75) Inventors: Birendra Prasad Srivastava, West Bengal (IN); Ranjana Srivastava, West Bengal (IN)

(73) Assignee: Micro-Dose Life Sciences LLC, Farmington Hills, MI (US)

( * ) Notice: Subject to any disclaimer, the term of this patent is extended or adjusted under 35 U.S.C. 154(b) by 6 days.

(21) Appl. No.: 13/057,293

(22) PCT Filed: May 18, 2009

(86) PCT No.: PCT/US2009/044322
§ 371 (c)(1),
(2), (4) Date: Feb. 3, 2011

(87) PCT Pub. No.: WO2010/030418
PCT Pub. Date: Mar. 18, 2010

(65) Prior Publication Data
US 2011/0171330 A1     Jul. 14, 2011

(30) Foreign Application Priority Data
Sep. 10, 2008   (IN) .......................... 2195/CHE/2008

(51) Int. Cl.
*A01N 65/00* (2009.01)

(52) U.S. Cl. ....................................................... 424/725
(58) Field of Classification Search .................... None
See application file for complete search history.

(56) References Cited

U.S. PATENT DOCUMENTS

| 6,210,738 | B1 | 4/2001 | Chen |
| 2003/0228359 | A1 | 12/2003 | Seko |
| 2006/0165812 | A1 | 7/2006 | Charron |

OTHER PUBLICATIONS

Joshi et al., "Swertia chirayita—an overview", Current Science, vol. 89, No. 4, p. 635-640, Aug. 25, 2005, (p. 636, col. 2, para 2; p. 635, col. 1, para 2).
Medpharm, German Homeopathic Pharmacopoeia, Nov. 3, 2003, 5th Edition, ISBN-10: 3887630955, ISBN 13: 978-3887630959.
http://enwikipedia.org/wiki/List_of_Eucalyptus_species.

*Primary Examiner* — Michael Meller
(74) *Attorney, Agent, or Firm* — Oakland Law Group PLLC

(57) ABSTRACT

According to at least one aspect of the present invention, a botanical anti-fever composition is provided. In at least one embodiment, the botanical composition comprises a therapeutically effective amount of admixture of parts or extracts of at least one plant species from each of genus *Baptisia* and genus *Swertia*. In at least one particular embodiment, the botanical composition contains *Baptisia Tinctoria*. In at least another particular embodiment, the botanical composition contains *Swertia Chirata*.

11 Claims, No Drawings

ANTI-FEVER BOTANICAL COMPOSITION AND USES THEREOF

BACKGROUND OF THE INVENTION

1. Field of the Invention

The present invention relates to a botanical composition useful as a preventative, alleviative, or remedy for treating one or more symptoms associated with fever.

2. Background Art

Fever is a common symptom of many medical conditions including infectious diseases such as influenza, common cold, HIV (human immunodeficiency virus), malaria, infectious mononucleosis, or gastroenteritis; various skin inflammations such as boils, pimples, acne, or abscess; immunological diseases such as lupus erythematosus, sarcoidosis, inflammatory bowel disease; tissue destruction involving hemolysis, surgery, or infarction; and conditions caused by an adverse reaction to medications such as antibiotics or sulfa drugs.

Fever, also known as pyrexia, is often described as an increase in internal body temperature to levels above the body's thermoregulatory set-point. Body temperature is regulated in the hypothalamus. Fever occurs in response to a pyrogen, a triggering substance. A pyrogen may be endogenous or exogenous to the body. The bacterial substance lipopolysaccharide (LPS) is an example of an exogenous pyrogen and certain cytokines produced by phagocytic cells are exemplary endogenous pyrogens.

People with fever experience fatigue, arthralgia, myalgia, anorexia, or delirium. Fever may further cause tachycardia, tachypnea, or an increase in metabolic rate. In situations where the underlying etiology for the fever symptom is inflammatory and or infectious, a fever left untreated may be fatal for patients who are weak and febrile.

Additionally, many synthetic drugs such as antibiotics are useful in treating bacterial infections associated with the underlying diseases; however, synthetic drugs often have side effects. By way of example, repetitive and prolonged use of antibiotics are known to induce antibiotics resistance in humans. Also, the use of antibiotics is severely restricted in pregnant patients.

As such, it is desirable to provide a natural remedy, with less side effects or use restrictions, for controlling fever symptoms and/or treating the underlying conditions associated with fever.

SUMMARY

According to at least one aspect of the present invention, a botanical anti-fever composition is provided. In at least one embodiment, the botanical composition comprises a therapeutically effective amount of admixture of parts or extracts of at least one plant species from each of genus *Baptisia* and genus *Swertia*. In at least one particular embodiment, the botanical composition contains *Baptisia Tinctoria*. In at least another particular embodiment, the botanical composition contains *Swertia Chirata*.

In at least one embodiment, the botanical composition further comprises parts or extracts from at least one plant species of a genus selected from the group consisting of genus *Azadirachta*, genus *Eucalyptus*, genus *Atropa*, and any combination thereof. In one particular embodiment, the botanical composition contains *Azadirachta Indica*. In another particular embodiment, the botanical composition contains *Eucalyptus Globulus*. In yet another particular embodiment, the botanical composition contains *Atropa Belladonna*.

According to another aspect of the present invention, a method for remedying one or more symptoms associated with fever in a subject is provided. In at least one embodiment, the method comprises administering to the subject a therapeutically effective amount of admixture containing parts or extracts of at least one plant species from each of genus *Baptisia* and genus *Swertia*.

DETAILED DESCRIPTION OF THE PREFERRED EMBODIMENT(S)

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

As used herein, "tincture" refers to an alcoholic extract or alcohol/water extract of a material, in particular, a herb, plant or tree component. The tincture used herein is typically the mother tincture of a component prepared according to the procedures of the Homœopathic Pharmacopœia of the United States ("HPUS"). Procedures for forming the mother tincture are also found in *German Homoeopathic Pharmacopoeia* ("GHP"), 5 edition (Nov. 3, 2003), Medpharm, ISBN-10: 3887630955, ISBN-13: 978-3887630959. This procedure from GHP is hereby incorporated by reference. When prepared according these procedures, a component is subject to the extracting solvent for an extended period of time. This results in tinctures with reproducible amounts of ingredients.

Ingredients of the botanical composition may be described by the Decimal Scale or the Centesimal Scale. The Decimal Scale is based on the principle that first potency (i.e., dilution) should contain ⅒th part of the original drug and each succeeding potency should contain ⅒th of the previous potency. In a variation, this scale is based on the mother tincture. The decimal potency is denoted by a suffix including the letter 'X' to the number indicating the potency. Therefore, the first potency is 1X, the second potency is 2X and so on. The Centesimal Scale is based on the principle that first potency (i.e., dilution) should contain 1/100th part of the original drug and each succeeding potency should contain 1/100th of the previous potency. The Centesimal scale is denoted by simply affixing the numerical after the name of the drug like Hamamelis 200, Millifolium 30, Nux. Vom. 200, etc. In a variation, this scale is also based on the mother tincture. These two systems for potency are also described in German Homoeopathic Pharmacopoeia ("GHP"), 5 edition (Nov. 3, 2003), Medpharm, ISBN-10: 3887630955, ISBN-13: 978-3887630959. These descriptions from GHP are hereby incorporated by reference.

As used herein and unless otherwise noted, the term a "therapeutically effective amount" refers to a dose of the botanical composition, when administered to a subject, that is able to cause a measurable change in fever reduction and amelioration of other fever-related symptoms. The exact value of a therapeutically effective amount varies based upon the sensitivity and size of each subject, and is readily determinable by one of skill in the art using conventional procedures for the routine administration of effective dose.

As used herein and unless otherwise mentioned, the term "efficacious material" refers to plant matter that is able to elicit a beneficial response when administered to a subject. For example, administration of the efficacious material to a mammal causes a physiological response that results in a lowering of body temperature. The effacacious material is optionally suspendable and or soluble in an extraction fluid or solution described herein such that the resulting extracts are able to elicit a similar beneficial response.

As used herein and unless otherwise noted, the term "extract" refers to a substance or composition obtained from one or more plant parts, regardless of whether the substance or composition is found external to the plant parts (i.e., an exudate). Chemical and/or physical action, as would be understood in the art, may be required to obtain the substance or composition from the plant parts. The extract may take the form of a solid, a liquid, or a gas. When the extract is in the liquid form, the extract is also referred to as a tincture.

Synthetic products presently used for the treatment of fever symptoms have many side effects and certain application limitations. The herbal kingdom offers few remedies for fever control. In natural therapy, certain herbal preparations are given mainly to boost the body's immune system. However, the use of these known herbal preparations has met with limited use since these preparations seldom give appreciable fever relief and or treatment for underlying disease conditions.

The present invention, in at least one embodiment, provides an improved composition having anti-fever properties, which not only provides relief particularly in acute febrile conditions but also helps in correcting the underlying pyrexia disorders. In at least one embodiment, the present invention provides an improved botanical composition having anti-fever properties which controls related symptoms such as body soreness, body pain, headache, nausea, cough, excessive sweat, and vomiting.

According to at least one aspect of the present invention, an anti-fever botanical composition is provided. In at least one embodiment, the anti-fever botanical composition comprises a therapeutically effective amount of an admixture containing parts of or extracts of at least one plant species from each of genus Baptisia and genus Swertia.

The species of the plant genus Swertia illustratively includes Swertia angustifolia, Swertia bimaculata, Swertia chinensis, Swertia chirayita, Swertia dilatata, Swertia hookeri, Swertia japonica, Swertia multicaulis, Swertia perennis, Swertia purpurascens, Swertia radiata, and Swertia tongluensis.

The species of the plant genus Baptisia illustratively includes Baptisia alba, Baptisia albescens, Baptisia arachnifera, Baptisia australis, Baptisia bicolor, Baptisia bracteata, Baptisia bushii, Baptisia calycosa, Baptisia cinerea, Baptisia confusa, Baptisia cuneata, Baptisia deamii, Baptisia elliptica, Baptisia fragilis, Baptisia fulva, Baptisia gibbesii, Baptisia hirsuta, Baptisia hugeri, Baptisia intercalate, Baptisia intermedia, Baptisia lactea, Baptisia aevicaulis, Baptisia lanceolata, Baptisia lecontei, Baptisia leucantha, Baptisia leucophaea, Baptisia macilenta, Baptisia megacarpa, Baptisia minor, Baptisia nuculifera, Baptisia nuttalliana, Baptisia oxyphylla, Baptisia pendula, Baptisia perfoliata, Baptisia pinetorum, Baptisia psammophila, Baptisia riparia, Baptisia saligna, Baptisia simplicifolia, Baptisia sphaerocarpa, Baptisia stricta, Baptisia sulphurea, Baptisia texana, Baptisia tinctoria, Baptisia vespertina, Baptisia viridis, Baptisia intermedia, and Baptisia variicolor.

In at least another embodiment, at least one species of Swertia contained within the anti-fever botanical composition is Swertia Chirata. Swertia Chirata is indigenous to temperate Himalayas at altitudes above 4000 feet from Kashmir, Nepal, and Bhutan. Swertia Chirata is sometimes found in other parts of India. Swertia Chirata is also known as Chirayata, Kirata-tikta, Kiryat-charayatah, Bhunimba, Bhuchiretta, Charayatah, Chiretta, Chiraita, Indian Gentian, Jwaran-thakah, Kirata, kiraita, Kiriath, Kiriyattu, Kiryat-charayatah, Mahatita, Nila-vemu, Nila-vembu, or Qasabuz-Zarirah. Swertia Chirata has been reported to be bitter tonic, stomachic, febrifuge, anthelmintic, laxative, antidiarrhoeic and antiperiodic. Swertia Chirata contains two bitter components: ophelic acid, an amorphous bitter principle, and chiratin, a yellow bitter glucoside.

In one refinement, the parts or extracts of a member of the genus Swertia (e.g. Swertia Chirata) are present in an amount of 0.0002 weight % to 0.5 weight % of the total weight of the botanical composition. In another refinement, the parts or extracts of a member of the genus Swertia are present in an amount of 0.0008 weight % to 0.06 weight % of the total weight of the botanical composition. The weight percentages are provided herein with the understanding that the balance is provided as a suitable liquid such as water. In another refinement, the parts or extracts of a member of the genus Swertia are present in an amount of 0.001 weight % to 0.02 weight % of the total weight of the botanical composition. In yet another refinement, the member of the genus Swertia is provided as a first potency 1X composition in an amount from about 0.1 to about 5% of the total weight of the botanical composition. In still another refinement, the member of the genus Swertia is provided as a first potency 1X composition in an amount from about 0.5 to about 2% of the total weight of the botanical composition. In yet another refinement, the member of the genus Swertia is provided as a first potency 1X composition in an amount from about 4 to about 12 parts by weight relative to the other components.

In at least one embodiment, at least one species of Baptisia contained within the anti-fever botanical composition is Baptisia Tinctoria. Also known as Wild Indigo or Indigoweed, Baptisia Tinctoria is generally anti-microbial and anti-catarrhal. Baptisia Tinctoria has been used to treat localized infections and catarrh in the ear, nose and throat. Baptisia Tinctoria has also been used in the treatment for laryngitis, tonsillitis, pharyngitis and catarrhal infections of the nose and sinus. Systemically, Baptisia Tinctoria may be helpful in the treatment of enlarged and inflamed lymph glands (lymphadenitis). *Baptisia Tinctoria* contains isoflavones, genistein, biochanin A, flavonoids, and alkaloids such as cytisine Coumarins Polysaccharides.

In at least one particular embodiment, the parts or extracts of a member of the genus *Baptisia* (e.g, *Baptisia Tinctoria*) are present in an amount of 0.0002 weight % to 0.5 weight % of the total weight of the botanical composition. In another refinement, the parts or extracts of a member of the genus *Baptisia* are present in an amount of 0.0008 weight % to 0.06 weight % of the total weight of the botanical composition. In another refinement, the parts or extracts of a member of the genus *Baptisia* are present in an amount of 0.001 weight % to 0.02 weight % of the total weight of the botanical composition. In yet another refinement, the member of the genus *Baptisia* is provided as a first potency 1X composition in an amount from about 0.1 to about 5% of the total weight of the botanical composition. In still another refinement, the member of the genus *Baptisia* is provided as a first potency 1X composition in an amount from about 0.5 to about 2% of the total weight of the botanical composition. In yet another refinement, the member of the genus *Baptisia* provided as a first potency 1X composition in an amount from about 2 to about 10 parts by weight relative to the other components.

In at least one embodiment, the botanical composition further includes parts or extracts of at least one species of plant genus *Eucalyptus*. In a refinement, the extract is provided as a tincture, and in particular, a tincture in about 60% alcohol/water (v/v). (v/v means volume/volume). Prior to forming the botanical composition of the invention, the tincture is optionally diluted with a suitable solvent (e.g., alcohol, water/alcohol). Exemplary species of the genus *Eucalyptus* is listed at http://enwikipedia.org/wiki/List_of_Eucalyptus_species, the entire content of which is incorporated herein by reference. *Eucalyptus* is a diverse genus of trees and a few shrubs.

*Eucalyptus* matures into single-stemmed forest trees, single-stemmed woodland trees, or multi-stemmed Mallees. The *Eucalyptus* trees vary in size ranging from 10 meters to 60 meters in height. *Eucalyptus* have very distinctive flowers and fruit (capsule). The flowers have numerous fluffy stamens which may be white, cream, yellow, pink or red. The appearance of *Eucalyptus* bark varies with the age of the plant, the manner of bark shed, the length of the bark fibers, or the degree of furrowing. Mature eucalypts put on an annual layer of bark, which contributes to the increasing diameter of the stems. By way of example, stringybark is characterized as having long-fibers and can be pulled off in long pieces; ironbark is hard, rough and deeply furrowed, and often has a dark red or even black color; tessellated has a bark that is broken up into many distinct flakes; box type has short fibers; and ribbon type has the bark coming off in long thin pieces but still loosely attached in some places. *Eucalyptus* is a tall, evergreen tree native to Australia and Tasmania. Among its various species, the blue gum is the one commonly grown in the US. The trunk of the blue gum, which grows to 300 feet high or more, is covered with peeling papery bark. The leaves on the young plant, up to 5 years old, are opposite, sessile, soft, oblong, pointed, and a hoary blue color.

Most *Eucalyptus* species are known to be antiseptic, antimicrobial, anti-spasmodic, and febrifuge. Most *Eucalyptus* medications are made from the greenish-yellow oil obtained from the mature leaves. The oil, or lozenges and cough drops made from it are useful for lung diseases, colds, and sore throat. The oil can also be used as a vapor bath for asthma and other respiratory ailments, and as an antiseptic bath additive. Its expectorant properties are useful for bronchitis. The oil is also said to be useful for pyorrhea and for burns and to prevent infection. An essential oil extracted from *Eucalyptus* leaves contains compounds that are natural disinfectants. *Eucalyptus* flowers produce a great abundance of nectar which is a food for insects, birds, and bats. *Eucalyptus* genus has many other uses which have made them economically important. The Karri and the Yellow box varieties are best known for providing desirable characteristics for use as ornament, timber, firewood and pulpwood. Fast growth also makes eucalypts suitable as windbreaks. Eucalypts draw a tremendous amount of water from the soil through the process of transpiration.

In at least another embodiment, the at least one species of the *Eucalyptus* contained within the botanical composition is *Eucalyptus Globulus*. Useful constituents of *Eucalyptus Globulus* include 1,8-cineole, terpineole, a-pinene, p-cymene, ledol, aromadendrene, viridoflorol; aldehydes, ketones, alcohols, polyphenolic acids; caffeic, ferulic, gallic, protocatechuic, eucalyptin, hyperoside, and rutin.

In at least one particular embodiment, the parts or extracts of a member of the genus *Eucalyptus* (e.g., *Eucalyptus Globulus*) are present in an amount of 0.0002 weight % to 0.5 weight % of the total weight of the botanical composition. In another refinement, the parts or extracts of a member of the genus *Eucalyptus* are present in an amount of 0.0008 weight % to 0.06 weight % of the total weight of the botanical composition. In another refinement, the parts or extracts of a member of the genus *Eucalyptus* are present in an amount of 0.001 weight % to 0.02 weight % of the total weight of the botanical composition. In yet another refinement, the member of the genus *Eucalyptus* is provided as a first potency 1X composition in an amount from about 0.1 to about 5% of the total weight of the botanical composition. In still another refinement, the member of the genus *Eucalyptus* is provided as a first potency 1X composition in an amount from about 0.5 to about 2% of the total weight of the botanical composition. In yet another refinement, the member of the genus *Eucalyptus* provided as a first potency 1X composition in an amount from about 2 to about 10 parts by weight relative to the other components.

In at least one embodiment, the botanical composition further comprises parts or extracts of at least one species of plant genus *Azadirachta*. Numerous species have been described in the genus but only two are currently recognized, *Azadirachta excelsa* (Jack Jacobs), and the economically important Neem tree, *Azadirachta indica* (A. Juss).

In at least another embodiment, at least one species of the *Azadirachta* contained within the botanical composition is *Azadirachta Indica*. In a refinement, the extract is provided as a tincture, and in particular, a tincture in about 60% alcohol/water (v/v). (v/v means volume/volume). Prior to forming the botanical composition of the invention, the tincture is optionally diluted with a suitable solvent (e.g., alcohol, water/alcohol). *Azadirachta Indica* is found in the Western Himalayas of India, and in Iran. It is cultivated in other parts of India and the tropical regions of the world such as Indonesia, Australia, and West Africa. *Azadirachta Indica* is considered to be a very valuable herb in Ayurvedic medicine and for a variety of folk applications. *Azadirachta Indica* is also known as Neem, Nimba, Nimb, Indian Lilac, Bead Tree, Holy Tree, Margosa Tree, Nim, Persian Lilac, Pride of China, Ravipriya, and Veppu. The root and bark of *Azadirachta Indica* are antiperiodic, astringent, and tonic. The bark of *Azadirachta Indica* is astringent, antiperiodic, antiviral, bitter, tonic, and vermifuge. The leaves of *Azadirachta Indica* are antiviral and discutient (an agent serves to disperse morbid matters). The flowers of *Azadirachta Indica* are stimulant, stomachic, and tonic. The fruit of *Azadirachta Indica* is anthelmintic, purgative, and emollient. The juice of *Azadirachta Indica* is anthelmintic. The oil extracted from the nuts of *Azadirachta Indica* is antiseptic and insecticidal. *Azadirachta Indica* has been used as a treatment for inflammatory and febrile diseases.

In at least one particular embodiment, the parts or extracts of a member of the genus *Azadirachta* (e.g., *Azadirachta Indica*) are present in an amount of 0.0002 weight % to 0.5 weight % of the total weight of the botanical composition. In another refinement, the parts or extracts of a member of the genus *Azadirachta* are present in an amount of 0.0008 weight % to 0.06 weight % of the total weight of the botanical composition. In another refinement, the parts or extracts of a member of the genus *Azadirachta* are present in an amount of 0.001 weight % to 0.02 weight % of the total weight of the botanical composition. In yet another refinement, the member of the genus *Azadirachta* is provided as a first potency 1X composition in an amount from about 0.1 to about 5% of the total weight of the botanical composition. In still another refinement, the member of the genus *Azadirachta* is provided as a first potency 1X composition in an amount from about 0.5 to about 2% of the total weight of the botanical composition. In yet another refinement, the member of the genus *Azadirachta* provided as a first potency 1X composition in an amount from about 4 to about 12 parts by weight relative to the other components.

In at least one embodiment, the botanical composition further comprises parts or extracts of *Atropa Belladonna*. In a refinement, the extract is provided as a tincture, and in particular, a tincture in about 60% alcohol/water (v/v). (v/v means volume/volume). Prior to forming the botanical composition of the invention, the tincture is optionally diluted with a suitable solvent (e.g., alcohol, water/alcohol). *Atropa Belladonna* is a perennial herbaceous plant with leaves and berries known to be toxic and hallucinogenic if overdosed. *Atropa Belladonna* flowers are solitary, bell-shaped, and dull brown to dark purple in color. *Atropa Belladonna* fruit is a sweet-tasting, black, shiny berry about the size of a cherry. *Atropa Belladonna* is a perennial branching herb growing to 5 meter tall, with 18 centimeter long ovate leaves. *Atropa Belladonna* is not a very hardy perennial and is sensitive to being transplanted. Germination requires several weeks in warm, moist, absolutely sterile soil, usually far from normal garden conditions. *Atropa Belladonna* is also known as Belladonna, deadly nightshade, Black cherry, and poison black cherry

*Atropa Belladonna* is an important source of atropine, which is an effective treatment for the effects of poisoning by cholinesterase inhibitors such as Parathion and Malathion. Atropine also reverses the effects of poisoning by nerve agents designed for chemical warfare. *Atropa Belladonna* extracts can also be found in some over-the-counter cold and flu medicines (in small amounts) due to its pseudoephedrine-like properties for clearing up nasal and other passages where mucus forms. Donnatal, or the generic Belladonna, is a FDA approved prescription pharmaceutical that contains natural belladonna alkaloids combined with Phenobarbital to provide peripheral anticholinergic/antispasmodic action and mild sedation. Donnatal contains belladonna alkaloids including atropine, hyoscyamine, and scopolamine. Belladonna alkaloids produce many effects in the body, including reduced muscle spasms in the digestive or urinary tract, an reduced fluid secretions from certain glands or organs. Donnatal is indicated and FDA approved as "possibly effective" for the treatment of IBS (irritable bowel syndrome), acute enterocolitis and as adjunctive therapy in the treatment of duodenal ulcer.

In at least one particular embodiment, the parts or extracts of a member of the genus *Atropa* (e.g., *Atropa Belladonna*) are present in an amount of 0.0000002 weight % to 0.005 weight % of the total weight of the botanical composition. In another refinement, the parts or extracts of a member of the genus *Atropa* are present in an amount of 0.0000008 weight % to 0.0006 weight % of the total weight of the botanical composition. In another refinement, the parts or extracts of a member of the genus *Atropa* are present in an amount of 0.000001 weight % to 0.0002 weight % of the total weight of the botanical composition. In yet another refinement, the member of the genus *Atropa* is provided as a third potency 3X composition in an amount from about 0.1 to about 5% of the total weight of the botanical composition. In still another refinement, the member of the genus *Atropa* is provided as a third potency 3X composition in an amount from about 0.5 to about 2% of the total weight of the botanical composition. In yet another refinement, the member of the genus *Atropa* provided as a third potency 3X composition in an amount from about 2 to about 8 parts by weight relative to the other components.

As set forth above, it should be appreciated that typically the active ingredients are provided in a carrier such as water. Therefore, this carrier will make up the balance. The ingredients may also be provided as a concentrate with the appropriate amounts being the part by weight set forth above (or by rescaling the weight percentages).

The efficacious materials of the anti-fever botanical composition may be derived from one or more selected plant parts of each of the genus *Swertia, Baptisia, Azadirachta, Eucalyptus,* or *Atropa*. The selected plant parts illustratively include barks, stems, leaves, roots, flowers, seeds, nuts, fruits, or any combinations thereof.

The selected plant parts may be directly used as the anti-fever composition or may be processed into a form illustratively including powder, tablet, capsule, liquid, gel, and food.

The selected plant parts may be processed to form extracts. The extracts may be processed individually for each plant species or the selected plant parts of multiple species may be processed together provided that process conditions are suitable for maintaining the effacacious materials contained within the plant parts. One skilled in the art should be able to decide the extraction conditions suitable for processing various plant genus and various plant species thereof by tuning parameters including dryness of starting plant material, extraction temperature, solvent polarity, and solvent acidity.

Extracts of various selected plant parts may be prepared using conventional methods. One exemplary extraction method is summarized below. In summary form, the method includes: (1) drying the selected plant parts and milling the dried plant parts to a fine powder; (2) mixing the plant powder to an extraction solvent; (3) removing the plant remnants by centrifugation and collecting the solvent supernatant; (4) removing the remaining solvent and water in the supernatant by rotary evaporation and drying. One of ordinary skill in the art would realize that the method may be modified appropriately, e.g., for the transition from a small-, or laboratory-, scale to a commercial-scale method. The drying process may not be needed for extraction purposes. Fresh plant material may be directly subjected to solvent extraction without the drying step. Dried plant parts do offer an advantage in terms of transport and storage of the crop; however, the activity of the extract from air-dried plants may be lower than the activity of freeze-dried extracts due to possible increase in breakdown of components in the air-dried counterparts.

The selected plant parts may be washed and cleaned and subject to a freeze-drying process. The freeze-drying process helps to reduce water content within the plant parts such that further processing of the plant parts may be facilitated. An exemplary freeze-drying process is shown in U.S. Pat. No. 6,210,738, the content of which in its entirety is incorporated herein with reference. In general, during the freeze-drying process, water does not exist as a liquid but rather as ice or vapor and sublimates directly from ice to vapor. As temperatures are increased at a controlled rate, the water in the selected plant parts sublimates. Once properly freeze-dried, the selected plant parts may be further processed alone or in combination with other plant parts in producing the botanical composition. Alternatively, the washed plant parts may be spray dried or heat dried at a temperature in the range of 50 to 70 degrees Celsius with or without vacuum.

The extraction solvent may be a mildly polar fluid. The "mildly polar" fluid means a fluid that is slightly to moderately polar, as would be understood in the art. Mildly polar as used herein means moderately irregular distribution of electrons that is characterized by a weak to average degree of hydrophilicity. A mildly polar fluid includes all straight chain and branched primary alcohols and chemical derivatives thereof, provided that the additional chemical groups do not destroy the polarity of the fluid or increase the polarity of the fluid to the level of water, which is expressly excluded from the definition of a mildly polar fluid. Preferred mildly polar fluids are liquids, such as the lower molecular weight, straight chain, primary alcohols (e.g., ethanol). Water is not a mildly polar fluid, but is a highly polar aqueous fluid. However, a mixture of water and a mildly polar fluid (e.g., ethanol) is itself a mildly polar fluid. An example of the latter fluid is 60% ethanol. A variety of mildly polar fluids, such as alcohols, may be used to extract efficacious materials from the selected plant parts, including methanol, ethanol, and isopropanol. When alcohol is used, the resulting product is an ethanolic extract.

In at least one embodiment, the anti-fever botanical composition further includes one or more general health promoting ingredients. The general health promoting ingredients may include, for example and not by way of limitation, agnus castus (*Vitex agnus-castus*), agrimony (*Agrimonia eupatoria*), anise (*Pimpinella anisum*), arjuna (*Terminalia arjuna*), arnica (*Arnica montana*), asafoetida (*Ferula assa-foetida*), astragalus (*Astragalus membranaceus*), avens (*Geum urbanum*), bay laurel (*Laurus nobilis*), Beleric myrobalan (*Terminalia belerica*), betony (*Stachys officinalis*), bilberry (*Vaccinium myritillus*), bistort (*Polygonum bistorta*), black cohosh (*Cimicifuga racemosa*), blackcurrant (*Ribes nigrum*), black haw (*Viburnum prunifolium*), bogbean (*Menyanthes trifoliata*), boldo (*Peumus boldus*), boneset (*Eupatorium perfoliatum*), buchu (*Barosma betulina*), bugleweed (*Lycopus virginicus*), burdock (*Arctium lappa*), calendula (*Calendula officinalis*), calumba (*Jateorhiza palmata*), cardamom (*Elletteria cardamomum*), cayenne (*Capsicum frutescens*), cerasee (*Momordica charantia*), cinchona (*cinchona*), cinnamon (*Cinnamomum verum*), clove (*Eugenia caryophyllata*), codonopsis (*Codonopsis pilosula*), coltsfoot (*Tussilago farfara*), comfrey (*Symphytum officinale*), common plantain (*Plantago major*), cornsilk (*Zea mays*), cowslip (*Primula veris*), crampbark (*Viburnum opulus*), damiana (*Turnera diffusa*), dandelion (*Taraxacum officinale*), devil's claw (*Harpagophytum procumbens*), echinacea (*Echinacea* spp.), eggplant (*Solanum melongena*), elder (*Sambucus nigra*), elecampane (*Inula helenium*), ephedra (*Ephedra sinica*), evodia (*Evodia rutaecarpa*), evening primrose (*Oenothera biennis*), eyebright (*euphrasia* spp.), fennel (*Foeniculum vulgare*), fumitory (*Fumaria officinalis*), galangal (*Alpinia officinarum*), garlic (*Allium sativum*), gentian (*Gentiana lutea*), ginger (*Zingiber officinale*), ginkgo (*Ginkgo biloba*), goat's rue (*Galega officinalis*), goldenrod (*Solidago vigaurea*), hanbane (*Hyoscyamus niger*), hops (*Humulus lupulus*), horsemint (*Monarda punctata*), Indian gooseberry (*Emblica officinalis*), jamaica dogwood (*Piscidia erythrina*), java tea (*Orthosiphon aristata*), jujube (*Ziziphus jujuba*), kantakari (*Solanum xanthocarpum*), lavender (*Lavandula officinalis*), lapacho (*Tabebuia* spp.), lemon (*Citrus limon*), lemon balm (*Melissa officinalis*), licorice (*Glycyrrhiza glabra*), linden (*tilia*), lobelia (*Lobelia inflata*), lycium (*Lycium chinense*), manioc (*Manihot esculenta*), meadowsweet (*Filipendula ulmaria*), milk thistle (*Carduus marianus*), Muira puama (*Liriosma ovata*), mullein (*Verbascum thapsus*), myrrh (*Commiphora molmol*), nettle (*Uritica dioica*), oats (*Avena sativa*), passionflower (*Passiflora incarnata*), patchouli (*Pogostemon cablin*), picrorrhiza (*Picrorrhiza kurroa*), prickly ash (*Zanthoxylum americanum*), purslane (*Protulaca oleracea*), rehmannia (*Rehmannia glutinosa*), rosemary (*Rosmarinus officinalis*), sarsaparilla (*smilax* spp.), schisandra (*Schisandra chinensis*), skullcap (*Scutellaria lateriflora*), slippery elm (*Ulmus rubra*), soapwort (*Saponaria officinalis*), spiny restharrow (*Ononis spinosa*), squaw vine (*Mitchella repens*), sweet basil (*Ocimum basilicum*), tea tree (*Melaleuca alternifolia*), tree lungwort (*Lobaria pulmonaria*), turmeric (*Curcuma longa*), thyme (*Thymus vulgaris*), vervain (*Verbena officinalis*), white willow (*Salix alba*), winter cherry (*Physalis alkekengi*), withania (*Withania somnifera*), wormwood (*Artemisia absinthium*), yarrow (*Achillea millefolium*), yellow dock (*Rumex crispus*) as well as vitamins, minerals and amino acids.

As explained earlier the botanical composition may be in the form of capsules, tablets, powder, syrups and liquids for the purpose of administration. In at least one embodiment, the anti-fever botanical composition further includes a pharmaceutically or physiologically acceptable formulation agent selected for suitability with the mode of administration. Acceptable formulation materials preferably are nontoxic to recipients at the dosages and concentrations employed. Suitable formulation agents are known to those skilled in the art of botanical and homeopathic compositions. Examples of such compositions include, but are not limited to, talc, sugar mannitol, lactose, pectin, dextrin, gelatin, starch, magnesium stearate, magnesium carbonate, sodium saccharine, cellulose, magnesium carbonate, sodium carboxymethylcellulose, a low melting wax, cocoa methylcellulose, tragacanth, butter, and the like. Naturally occurring forms of these materials are most desirable. In one refinement, the botanical composition includes an agent in an amount of about 5 weight % to about 80 weight %.

The effectiveness of the anti-fever botanical composition is determined by one skilled in the art depending upon, for example, the intended route of administration, delivery format, and desired dosage. See for example, Remington's Pharmaceutical Sciences. Such compositions may influence the physical state, stability, rate of in vivo release, and rate of in vivo clearance of the plant extracts, such as the mildly polar extracts of plant parts.

In at least another aspect of the present invention, a method for reducing one or more fever related symptoms and or for controlling underlying disease conditions is provided. The fever related symptoms illustratively include elevated body temperatures, cough, body chill, body ache, headache, nausea, vomit, and excessive sweat. The underlying disease conditions illustratively include Q fever, rheumatic fever, dengue fever, dengue hemorrhagic fever, typhoid fever, and other infectious or inflammatory conditions.

Q fever is caused by infection with *Coxiella burnetii*. The organism is found in cattle, sheep, goats or other domestic mammals. The infection results from inhalation of contaminated particles in the air, or from contact with the vaginal mucus, milk, feces, urine or semen of infected animals. The most common manifestation is flu-like symptoms with abrupt onset of fever, malaise, profuse perspiration, severe headache, muscle pain, joint pain, dry cough, chills, and gastrointestinal symptoms such as nausea, vomiting, and diarrhea. The fever lasts approximately 7 to 14 days. During the course, the disease may progress to atypical pneumonia, which can result in a life threatening acute respiratory distress syndrome. The chronic form of the Q fever is similar to the inflammation of the inner lining of the heart (endocarditis), which can occur after months or decades following the infection. It is usually deadly if untreated. Treatment of the Q fever with antibiotics may be severely discounted in pregnant patients or who are otherwise resistant to the antibiotics.

Rhematic fever is an inflammatory disease which may develop after a Group A streptococcal infection. Rheumatic fever is common worldwide and responsible for many cases of damaged heart valves. In the Western countries, it became fairly rare since the 1960s, probably due to widespread use of antibiotics to treat streptococcus infections. While it is far less common in the United States since the beginning of the 20th century, there have been a few outbreaks since the 1980s. Although the disease seldom occurs, it is serious and has a mortality of 2-5%. Rheumatic fever primarily affects children between ages 6 and 15 years and occurs approximately 20 days after strep throat or scarlet fever. The rate of development of rheumatic fever in individuals with untreated strep infection is estimated to be 3%. Persons who have suffered a case of rheumatic fever have a tendency to develop flare-ups with repeated strep infections. Heart complications may be long-term and severe, particularly if valves are involved.

Dengue fever and dengue hemorrhagic fever (DHF) are acute febrile diseases, found in the tropics and Africa, with a geographical spread similar to malaria. Unlike malaria which is often eradicated in major cities, dengue is mainly found in urban areas of developed tropical nations, including Singapore, Taiwan, Indonesia, and Brazil. Dengue is transmitted to humans by the *Aedes aegypti* mosquito. This infectious disease is manifested by a sudden onset of fever, with severe headache, muscle and joint pain and rashes. The dengue rash is characteristically bright red petechiae and usually appears first on the lower limbs and the chest; in some patients, it spreads to cover most of the body. There may also be gastritis with some combination of associated abdominal pain, nausea, vomiting or diarrhea. The classic dengue fever lasts about six to seven days, with a smaller peak of fever at the trailing end of the disease (the so-called "biphasic pattern"). Clinically, the platelet count will drop until the patient's temperature is normal.

Typhoid fever, also known as enteric fever or bilious fever, is a disease caused by the bacterium *Salmonella enterica* serovar Typhi. The disease is transmitted by the fecal-oral route. The bacterium is a Gram-negative short *bacillus* that is motile due to its peritrichous flagella. Typhoid fever is characterized by a sustained fever as high as 40 degrees Celsius or 104 degrees Fahrenheit, profuse sweating, gastroenteritis, and diarrhea. Untreated typhoid fever may develop through the course of bradycardia, abdominal pain, intestinal hemorrhage, and eventually typhoid state. Typhoid fever in most cases is not fatal. Antibiotics, such as ampicillin, chloramphenicol, and ciprofloxacin, have been commonly used to treat typhoid fever. When untreated, typhoid fever may persist for weeks or months. Death occurs in between 10 to 30 percent of the untreated cases.

In another embodiment of the present invention, a method of alleviating one or more symptoms of fever in a subject (i.e., a human patient) is provided. The method of this embodiment comprises administering to the subject a therapeutically effective amount of the botanical compositions set forth above. The dose of the composition may vary according to the particular conditions of the patients.

In at least one embodiment, the method includes administering to a subject a therapeutically effective amount of the botanical compositions set forth above. In one refinement, an amount from about 3.0 to about 6.0 ml of the botanical composition is administered to the subject per day. In another refinement, an amount from about 6.0 to about 12 ml of the botanical composition is administered to the subject per day. In another refinement, an amount from about 9.0 to about 18 ml of the botanical composition is administered to the subject per day. The composition will be administered to a subject for a sufficient number of day to alleviate a symptom related to fever. Typically, this time period is from about 3 days to about 6 months. In another refinement, the time period is from about 5 days to about 3 months. In still another refinement, the time period is from about 7 days to about 1 month.

The threshold for fever that should prompt evaluation is arbitrary and depends on the patient setting and condition. For example, an otherwise healthy patient with a single fever to 38.3 degrees Celsius immediately after routine uncomplicated abdominal surgery would rarely require significant evaluation. In contrast, an elderly patient with unexplained delirium and temperature to 38.0 degrees Celsius requires a more thorough evaluation. In addition, some patient populations including the elderly are known to have lower temperatures at baseline or the set-point.

The botanical compositions as set forth above may be administered orally, parentally such as intravenously, by intramuscular injection, by intraperitoneal injection, or transdermally. The exact dose of the botanical composition required may vary from subject to subject, depending on the age, weight, general condition of the subject, the severity of disease conditions associated with fever, the mode of administration, and the like. An appropriate dose is readily determined by one of ordinary skills in the art using only routine experimentation given the teachings herein.

For oral administration, fine powders or granules may contain diluting, dispersing, and/or surface active agents, and may be presented in water or in a syrup, in capsules or sachets in the dry state or in a non-aqueous solution or suspension wherein suspending agents may be included, in tablets wherein binders and lubricants may be included, or in a suspension. Where desirable or necessary, flavoring, preserving, suspending, thickening, or emulsifying agents may be included. Tablets and granules may further be coated.

The following examples illustrate the various embodiments of the present invention. Those skilled in the art will recognize many variations that are within the spirit of the present invention and scope of the claims.

1. Preparation—Exemplary Botanical Composition Formulation

Respective tinctures are added in the following formula: 8 drops of the tincture of *Swertia Chirata*; 6 drops of the tincture of *Baptisia Tinctoria*; 8 drops of the tincture of *Azadirachta Indica*; 8 drops of the tincture of *Eucalyptus Globulus*; and 5 drops of the tincture of *Atropa Belladonna*. The tincture mixture is brought up to a final volume of 30 milliliters with distilled water and comprise a botanical composition.

2. Study Relief of Signs and Symptoms Associated with Fever in Pediatric Patients The prime objective of the study was to establish the safety and efficacy of a botanical composition as described in Example 1, above. Pediatric patients diagnosed with fever fulfilling the inclusion/exclusion criteria were enrolled in the study. A total of 39 patients participated in the study and were available for follow-up. These same patients are included in the report.

Methods

The investigational botanical composition was provided in suspension dosage form for oral administration. Depending upon the patient's medical condition any of the following schedules were utilized at the discretion of the investigational monitor: a) 5 drops every 2 hrs (0-1 year old), b) 10 drops every 2 hrs (1-2 years old) or c) 15 drops every 2 hrs (2-5 years old) in the course of a 24 hour period.

The investigation enrolled approximately 40 pediatric patients up to 5 years of age, diagnosed with a fever up to 102 degrees Fahrenheit. Other than the fever manifestation, the patients were also required to be present within 12 hours of initial onset and free from noticeable systemic or functional diseases.

The patients were dosed, according to the schedule shown above, for 24 hours and follow-up evaluation was performed at least once within 24 hours. The response rate was calculated as the number of responders divided by the number of patients who qualified for efficacy analysis. Safety was analyzed based on evaluation of adverse event rates and WHO toxicity grade laboratory and clinical parameters.

Results

The overall response to the investigational botanical product was 83.3%. Approximately 5% showed no change in symptoms and approximately 8% showed an aggravation of their symptoms. The study found the botanical investigational product was effective in reducing fever. In addition patients showed a reduction in fever related symptoms including: malaise, headache, body ache. A summary of individual symptoms and improvement are shown below in Table I.

TABLE I

Efficacy Results for Individual Symptoms

| | Symptom | Number of Patients with Symptom | Aggravation | No Change | Amelioration | Percent of Amelioration |
|---|---|---|---|---|---|---|
| a | Fever | 37 | 3 | 2 | 32 | 86.5% |
| b | Malaise | 34 | 3 | 2 | 29 | 85.3% |
| c | Headache | 35 | 3 | 3 | 29 | 82.9% |
| d | Body ache | 34 | 3 | 4 | 27 | 79.4% |
| e | Dry cough | 33 | 3 | 5 | 25 | 75.8% |
| f | Sneezing | 33 | 3 | 2 | 28 | 84.8% |
| g | Nasal discharge | 32 | 3 | 2 | 27 | 84.4% |
| h | Nausea & Vomiting | 17 | 3 | 2 | 12 | 70.6% |
| i | Weakness | 39 | 3 | 2 | 36 | 92.3% |
| j | Further complications | 0 | 0 | 0 | 0 | 0 |
| Average Percentage of Amelioration | | | | | | 83.3% |

The botanical antipyretic treatment is effective in reducing fever in pediatric patients less than 5 years old. The botanical combination is also active in reducing symptoms associated with fever including malaise, headache and body aches. The treatment was especially effective in reducing general weakness. However, the treatment although effective was not found to be as effective against a dry cough or nausea and vomiting. The preliminary overall effectiveness of the botanical antipyretic treatment was determined in the absence of a placebo group. Additional controlled studies are indicated including older children and adults.

While embodiments of the invention have been illustrated and described, it is not intended that these embodiments illustrate and describe all possible forms of the invention. Rather, the words used in the specification are words for description rather than limitation, and it is understood that various changes may be made without departing from the spirit and scope of the invention.

What is claimed:

1. A botanical composition for reducing fever consisting essentially of: a therapeutically effective amount of an admixture of extracts of *Swertia Chirata* and extracts of *Baptisia Tinctoria*.

2. The botanical composition of claim 1, wherein said extracts of *Baptisia Tinctoria* are about 0.0002 to 0.5 percent by weight of the total weight of the botanical composition.

3. The botanical composition of claim 1, wherein said extracts of *Swertia Chirata* are about 0.0002 to 0.5 percent by weight of the total weight of the botanical composition.

4. The botanical composition of claim 1 being formulated into a dosage form selected from the group consisting of tablets, capsules, liquids, powders, pills, and confectionary bars.

5. A botanical composition for reducing fever, consisting essentially of a therapeutically effective amount of an admixture of extracts of *Swertia Chirata*, extracts of *Baptisia Tinctoria* and extracts of a species selected from the group consisting of *Azadirachta Indica, Eucalyptus Globulus, Atropa Belladona*, and combinations thereof.

6. The botanical composition of claim 5, wherein said extracts of *Baptisia Tinctoria* are about 0.0002 to 0.5 percent by weight of the total weight of the botanical composition.

7. The botanical composition of claim 5, wherein said extracts of *Swertia Chirata* are about 0.0002 to 0.5 percent by weight of the total weight of the botanical composition.

8. The botanical composition of claim 5, wherein said extracts of *Eucalyptus Globulus* are about 0.0002 to 0.5 percent by weight of the total weight of the botanical composition.

9. The botanical composition of claim 5, wherein said extracts of *Atropa Belladona* are about 0.0000002 to 0.005 percent by weight of the total weight of the botanical composition.

10. The botanical composition of claim 5, wherein said extracts of *Azadirachta Indica* are about 0.0002 to 0.5 percent by weight of the total weight of the botanical composition.

11. The botanical composition of claim 5 being formulated into a dosage form selected from the group consisting of tablets, capsules, liquids, powders, pills, and confectionary bars.

* * * * *